(12) United States Patent
Munro, III et al.

(10) Patent No.: US 7,530,941 B2
(45) Date of Patent: May 12, 2009

(54) X-RAY AND GAMMA RAY EMITTING TEMPORARY HIGH DOSE RATE BRACHYTHERAPY SOURCE

(75) Inventors: John J. Munro, III, North Andover, MA (US); Matthew R. Hollows, Westminster, MA (US)

(73) Assignee: Best Medical International, Inc., Springfield, VA (US)

( * ) Notice: Subject to any disclaimer, the term of this patent is extended or adjusted under 35 U.S.C. 154(b) by 607 days.

(21) Appl. No.: 10/770,346

(22) Filed: Feb. 2, 2004

(65) Prior Publication Data

US 2004/0254418 A1     Dec. 16, 2004

Related U.S. Application Data

(60) Provisional application No. 60/477,467, filed on Jun. 10, 2003.

(51) Int. Cl.
*A61N 5/00* (2006.01)
(52) U.S. Cl. .......................................... 600/8
(58) Field of Classification Search ................... 600/1–8
See application file for complete search history.

(56) References Cited

U.S. PATENT DOCUMENTS

| | | |
|---|---|---|
| 1,753,287 A | 4/1930 | Failla |
| 1,954,868 A | 4/1934 | Failla et al. |
| 2,322,902 A | 6/1943 | Wappler |
| 2,429,438 A | 10/1947 | Wappler |
| 2,546,761 A | 3/1951 | Loftus |
| 3,060,924 A | 10/1962 | Rush |
| 3,351,049 A | 11/1967 | Lawrence |

(Continued)

FOREIGN PATENT DOCUMENTS

EP     1 232 770 A1     8/2002

(Continued)

OTHER PUBLICATIONS

R K Das, V Mishra, H Perera, A S Meigooni and Jeffrey F Williamson: "A secondary air kerma strength standard for Yb-169 interstitial brachytherapy sources"; Phys. Med. Biol. vol. 40 (1995), pp. 741-756, XP-001205094; IOP Publishing Ltd.; Printed in the UK.

(Continued)

*Primary Examiner*—Samuel G Gilbert
(74) *Attorney, Agent, or Firm*—Muirhead & Saturnelli, LLC (57) ABSTRACT

Radioactive sources are manufactured for treating a tumor or cancerous area occurring around a conduit or duct in the body by emitting X-rays to destroy or reduce the tumors. The sources contain ytterbium which is substantially enriched in $^{168}$Ytterbium and which is activated by exposure to neutron flux so as to contain a minor, but significant, fraction of X-ray and gamma-emitting $^{169}$Ytterbium. The radioactive $^{169}$Ytterbium source is inserted through a catheter or applicator or needle to the site of the cancer where it is maintained in position for a period of time to reduce the occurrence of cancer. The ytterbium also acts as an X-ray-opaque marker to facilitate external visualization of the sources during their delivery to the treatment site. The sources are encased in a shell to prevent direct contact of the radioactive material with human tissue. This encapsulation may be formed by welding a pair of end caps to a tubular member.

51 Claims, 2 Drawing Sheets

U.S. PATENT DOCUMENTS

| | | | |
|---|---|---|---|
| 3,438,365 | A | 4/1969 | Packer et al. |
| 3,669,093 | A | 6/1972 | Sauerwein et al. |
| 4,815,449 | A | 3/1989 | Horowitz |
| 4,881,937 | A | 11/1989 | van't Hooft et al. |
| 5,084,002 | A | 1/1992 | Liprie |
| 5,395,300 | A * | 3/1995 | Liprie ............................ 600/3 |
| 6,099,457 | A | 8/2000 | Good |
| 6,183,409 | B1 | 2/2001 | Armini |
| 6,716,156 | B2 * | 4/2004 | Menuhr et al. .................. 600/8 |

FOREIGN PATENT DOCUMENTS

| | | |
|---|---|---|
| RU | 2 158 170 C1 | 10/2000 |
| WO | WO 00/09212 | 2/2000 |

OTHER PUBLICATIONS

W. A. Bell, J. G. Tracy: "Stable Isotope Inventory Requirements and Enrichment Capabilities"; prepared by Oak Ridge National Laboratory/Martin Marietta, No. TM-9809, Dec. 1985; pp. 1-53, p. 11; table 1, XP002322580; National Technical Information Service, U. S. Department of Commerce, 5285 Port Royal Road, Springfield, Virginia 22161.

Barbara Fisher, MD, Arthur Porter, MD, Robert Barnett, PhD, Darcy Mason, MSc, Ewa Papiez, MSc, Jerry Battista, PhD: "First Clinical Application of a New Brachytherapy Source—Ytterbium-169"; Endocurietherapy/Hyperthermia Oncology, ISSN 8756-1687, Oct. 1993, pp. 195-199, XP009045136.

D. L. D. Mason, J. J. Battista, R. B. Barnett, A. T. Porter: "Ytterbium-169: Calculated physical properties of a new radiation source for brachytherapy"; Medical Physics, vol. 19, No. 3, May/Jun. 1992, pp. 695-703, XP002322581; © 1992 Am. Assoc. Phys. Med.

Piemattei, A., et al., "Implantation guidelines for $^{169}$Yb seed interstitial treatments," Phys. Med. Biol. 40 (1995) 1331-1338.

United States Nuclear Regulatory Commission, NRC Information Notice No. 95-58, Dec. 18, 1995.

Hetherington, E.L.R., et al., "The Production of Ytterbium-169 Radiography Sources in a High Flux Reactor," Australian Atomic Energy Commission, AAEC/E306, Feb. 1974.

"Security of Radioactive Sources," International Atomic Energy Commission, Proceedings of international conference, Vienna, Austria, Mar. 10-13, 2003 (p. 38).

"Ytterbium 169 gammatrack industrial sources," available at http://www.mdsnordion.com/agiris/agirisE/MainframesE/Ytterbium169.html, visited Mar. 25, 2008.

"Pipeline Crawler Systems", High Technology Sources, Ltd., available at http://hightechsource.co.uk/equipment/pipelinecrawlersystems.html, visited Mar. 25, 2008.

* cited by examiner

Figure 1

Figure 2:  Radial Dose Function

Figure 3: Attenuation in Lead

Figure 4

X-RAY AND GAMMA RAY EMITTING TEMPORARY HIGH DOSE RATE BRACHYTHERAPY SOURCE

This application claims the priority of U.S. Provisional Application No. 60/477,467, dated Jun. 10, 2003, the entire contents of which are incorporated herein by reference.

FIELD OF THE INVENTION

The present invention relates to the field of brachytherapy, which is the field of radiation treatment of cancerous tissue that would occur in the body by placing radiation sources in or near the cancerous tissue.

The present invention is directed to temporary application of high dose rate X-ray and gamma-emitting sources. More particularly the invention is directed to sources containing $^{169}$Ytterbium as the X-ray and gamma-emitting source and to methods of producing sources for temporary application.

BACKGROUND OF THE INVENTION

Various techniques have been developed to treat tumors in the body. In general, the use of radiation as a means to reduce or eliminate malignancy has been known for many years.

The type of radiation treatment of malignant tumors often performed involves directing a beam of radiation from a point external to the patient's body onto the area of the body in which the tumor is located, for the purpose of shrinking and ultimately destroying the tumor. This technique is known as "teletherapy" or external beam radiation therapy. Such treatment exposes normal healthy tissue to the high dosage of radiation in the beam and consequently subjects this normal healthy tissue to potential injury.

Brachytherapy is a method of radiation treatment of cancerous tissue in which the radiation source is placed in or near the cancerous tissue. Brachytherapy treatment permits administration of higher radiation dose to the tumor while reducing the exposure of surrounding normal healthy tissues.

Brachytherapy came into use as a treatment tool for cancer soon after the discovery of radium by Marie Curie in 1898. Goldberg and London used it for the treatment of facial basal cell carcinomas in 1903 with surface applicators.

Failla, in U.S. Pat. Nos. 1,753,287 and 1,954,868, describes a method of fabricating sealed sources of radium and their use for therapeutically treating cancer or tumors or other diseases.

Brachytherapy can be applied to cancer either by permanent implantation or by temporary application of removable sources. A variety of radionuclides and methods for permanent implantation have been described.

Wappler, in U.S. Pat. Nos. 2,322,902 and 2,429,438, describes a method of manufacturing sealed sources of "radium emanation intended for implantation into a human body for the purpose of producing certain beneficial effects upon cancerous growths and the like." Lawrence, in U.S. Pat. No. 3,351,049, describes the manufacture of permanently implantable seeds using $^{125}$Iodine, $^{131}$Cesium and $^{103}$Palladium. Packer, et al., in U.S. Pat. No. 3,438,365, describe the structure, method of manufacture, and use of seeds for implantation containing radioactive isotopes of xenon for use in cancer radiation therapy. Horowitz, in U.S. Pat. No. 4,815,449, describes a delivery system for implanting a plurality of seeds into living tissue in a predetermined array configuration.

Permanent implantation results in the radioactive sources, or seeds, being left in the body in perpetuity, delivering their radiation dose until the radioactive material in the source has completely decayed away. This is not appropriate for some patients.

Temporary brachytherapy is a process whereby the radioactive sources are placed into the body, usually using an applicator, such as a needle, catheter or other tubular apparatus, for a period of time to deliver the requisite radiation dose, following which the sources are removed. In general, applicators are prepositioned in the patient, and sources are later temporarily placed within them. This procedure is known in the field as "afterloading."

Loftus, in U.S. Pat. No. 2,546,761, describes an applicator used to temporarily deliver the radiation from a radium source for the treatment of lymphoid tissue in the nasopharynx. Rush, in U.S. Pat. No. 3,060,924, describes an apparatus for temporarily applying radioactive substances within the body such as the cervical-vaginal cavities.

Originally, temporary brachytherapy was performed using a technique that became known as "low dose rate brachytherapy." Using this technique, radioactive sources would be applied to provide a dose rate of 0.4 to 2 Gy/hour to the tumor. Using these techniques, treatment would require up to several days, during which period the patient would remain hospitalized. Low dose rate techniques utilized a variety of radioactive isotopes, including $^{125}$Iodine, $^{137}$Cesium, $^{198}$Gold and $^{192}$Iridium.

"High dose rate brachytherapy," developed later, uses a source that provides dose rates in the range of 2-7 Gy/minute. This technique permits the treatment to be performed in less than an hour and without hospitalizing the patient. These treatments are typically delivered in multiple fractions over several days or weeks.

High dose rate brachytherapy is particularly appealing to facilities with large patient populations, where treatment by low dose rate brachytherapy would require prolonged hospitalizations. Treating these patients as outpatients, using multiple fraction treatment regimens of high dose rate brachytherapy, is appealing to the patients. Free-standing radiation therapy centers that do not provide hospital rooms also find high dose rate brachytherapy appealing.

Sauerwein, et al., in U.S. Pat. No. 3,669,093, describe an apparatus for performing high dose rate brachytherapy using an afterloading source. Van't Hooft, et al., in U.S. Pat. No. 4,881,937, describe a method for performing high dose rate treatment to a part of the body. Liprie, in U.S. Pat. No. 5,084,002, describes a high dose rate $^{192}$Iridium source for the treatment of cancer.

Current high dose rate brachytherapy is performed exclusively using $^{192}$Iridium sources which have an initial activity of ~10 Curies. Such sources produce dose rates of 6.8 Gy/min at 1 centimeter. Using such a source, high dose rate treatments are typically performed for 5-15 minutes.

$^{192}$Iridium sources can be readily produced from substantially pure iridium. Relatively small amounts of iridium (e.g., a small volume) can be irradiated to a relatively high level of radioactivity in a relatively small size. $^{192}$Iridium has been produced by prior art techniques in a nuclear reactor with dosages of up to 10 curies in a diameter small enough to allow a source wire diameter of about 1 millimeter (mm). Liprie describes one technique for achieving this in U.S. Pat. No. 5,395,300.

$^{192}$Iridium sources have a significant disadvantage. $^{192}$Iridium sources emit very high energy gamma radiation, with principal energies in the range of 300-600 keV, and with some emissions in excess of 1000 keV. Consequently, these sources require an enormous amount of shielding. A typical $^{192}$Iridium treatment room requires more than 50 mm of lead shielding or 0.6 meters of concrete shielding to provide radiation protection to the clinical personnel and others in the vicinity of the treatment room. As a result, building a facility designed to use this type of source represents a very significant investment.

An exemplary radionuclide for the treatment of malignant tumors would emit x-rays and/or gamma rays with energy in the range of 50 keV to 70 keV, with little x-ray or gamma ray emission outside this range. This energy range will provide a favorable dose distribution surrounding a tumor, while enabling the source to be adequately shielded by a relatively thin amount (~1 cm) of lead. $^{169}$Ytterbium meets this criterion.

The use of $^{169}$Ytterbium for the treatment of malignant tumors has been investigated before.

Mason, et al., in Medical Physics 19 (3) 695-703 (1992) describe the calculated physical properties of a $^{169}$Ytterbium source. They discuss the theoretical possibility of achieving sources with activity concentrations of 350 GBq/mm$^3$ (<10 Ci/mm$^3$). However, the authors report only theoretical results, and do not provide any data relating to achieving high activity in these sources.

Fisher, et al., in Endocurietherapy/Hyperthermia Oncology, 9, 195-199 (1993) describe the first clinical application of a $^{169}$Ytterbium low dose rate brachytherapy source.

Perera, et al, in International Journal of Radiation Oncology, Biology and Physics, 28 (4) 953-970 (1994) describe the dosimetric characteristics, air-kerma strength calibration and Monte Carlo simulation for a new $^{169}$Ytterbium brachytherapy source. The basis of the work of this paper was interstitial seeds used for low dose rate brachytherapy. However, the authors also describe an "experimental high dose rate source." However, this source would not be considered a high dose rate brachytherapy source by current standards. It was significantly larger than the conventional high dose rate (HDR) sources in commercial use (2.5 mm in diameter vs. 1 mm in diameter for current high dose rate sources). This source was also much lower in activity than the typical sources currently used for high dose rate brachytherapy (86 millicuries vs. 10 curies for current high dose rate sources).

Das, et al., in Phys. Med. Biol., Vol. 40, pp 741-756, (1995) report on measurements of a HDR-type source. The actual activity of the source was not reported, but the HDR-type source was described as "low strength" and reference was made to 5-20 millicuries.

High activity $^{169}$Ytterbium sources have been produced for industrial use. Isotope Products, Inc. has registered a $^{169}$Ytterbium source with dimensions of 1 mm diameter and 3.6 mm length and a maximum activity of 5 curies. This source was much lower in activity than the typical sources currently used for high dose rate brachytherapy (10 curies).

MDS Nordion describes a $^{169}$Ytterbium source with an active diameter of 0.6 mm and length of 0.6 mm and a nominal activity of 1 curies and another with an active diameter of 1.0 mm and length of 1.0 mm with a nominal activity of 3 curies. These sources are also much lower in activity than the typical sources currently used for high dose rate brachytherapy (10 curies).

Thus, it would be desirable to have methods and materials for making $^{169}$Ytterbium available as a high dose rate temporary X-ray and gamma ray source. Such materials should be capable of being fabricated into sources small enough to fit in a delivery catheter, but with enough activity to enable therapy within a reasonable amount of time.

Such a method could provide a new and improved radioactive source for in vivo localized radioactive treatment of malignant tumors and could be exploited to provide high dose rates and a more favorable energy spectrum for better radiation protection properties and certain clinical benefits.

It is also desirable to provide an improved design and method of fabrication for a high dose radioactive source for use in interstitial, intraluminal and/or intracavitary brachytherapy.

It is also desirable to provide a radioactive source for treatment that is cost effective.

SUMMARY OF THE INVENTION

According to the present invention, a $^{169}$Ytterbium radioactive source to be used for temporary brachytherapy is encapsulated prior to activation in a material that does not contain unacceptable amounts of isotopes that, when irradiated by neutron flux, would be transmuted to radioactive isotopes that emit undesirable radiations for the treatment of tumors, or if transmuted into radioactive isotopes that emit undesirable radiations, have such short half-lives that they will have inconsequential activities shortly after irradiation.

According further to the present invention, a $^{169}$Ytterbium radioactive source includes a pellet having a size of 2 mm$^3$ or less, where the pellet includes ytterbium and has an activity greater than 10 curies and an activity concentration of at least 10 curies/mm$^3$. The source may further include a capsule encasing the pellet. The ytterbium may includes at least 15% $^{168}$Ytterbium. The pellet may have a density of 5 g/cm$^3$ or greater and include ytterbium oxide enriched with at least 15% $^{168}$Ytterbium oxide, and the source may include a biocompatible capsule encasing the pellet. The pellet may have a density of at least 6 g/cm$^3$, 7 g/cm$^3$, 8 g/cm$^3$, or 9 g/cm$^3$. The source may have an activity concentration of at least 20 curies/mm$^3$ or of at least 30 curies/mm$^3$.

According further to the present invention, a $^{169}$Ytterbium radioactive source includes a pellet including $^{168}$Ytterbium and having a volume less than 2 mm$^3$, where the pellet, having once been activated to an activity greater than 10 curies and an activity concentration of greater than 10 curies/mm$^3$ and decayed by more than one halflife, contains sufficient remaining unactivated $^{168}$Ytterbium to permit reactivation to an activity greater than 10 curies, and an activity concentration of greater than 10 curies/mm$^3$ by exposure to a flux of thermal neutrons of a nuclear reactor. The pellet may include at least 50% ytterbium and the ytterbium includes at least 15% $^{168}$Ytterbium. The pellet may have a density greater than 5 g/cm$^3$, 6 g/cm$^3$, 7 g/cm$^3$, 8 g/cm$^3$, or 9 g/cm$^3$. The pellet may have a volume of an amount that is at most 1.5 mm$^3$ or at most 1 mm$^3$. The pellet may include powdered ytterbium or ytterbium oxide pressed into a solid form. The powdered ytterbium oxide may be formed into a pellet by sintering or hot isostatic pressing. The pellet may include ytterbium in an amount that is at least 60%, at least 70%, at least 80%, or at least 90%. The ytterbium may include $^{168}$Ytterbium in an amount that is at least 20%, at least 30%, at least 40%, at least 50%, at least 60%, at least 70%, at least 80%, or at least 90%. The source may further including a capsule encasing the pellet. The capsule may not exhibit a significant amount of radioactive emission outside a predetermined energy range. The capsule may not exhibit a significant amount of radioactive emission having an energy greater than 310 keV or may not exhibit a significant amount of radioactive emission having an energy greater than 100 keV or may not exhibit a significant amount of radioactive emission having an energy greater than 310 keV and a half life greater than about 1 day or may not exhibit a significant amount of radioactive emission having an energy greater than 100 keV and a half life greater than about 1 day. The capsule may include one or more materials selected from aluminum, copper, vanadium, nickel, iron, titanium, silicon, carbon, oxygen, and alloys and compounds of the above. The source, when irradiated by a neutron flux, may not exhibit a significant amount of radioactive emission outside a predetermined energy range. The source, when irradiated by a neutron flux, may not exhibit a significant amount of radioactive emission having an energy greater than 310 keV or may not exhibit a significant amount of radioactive emission having an energy greater than 100 keV or may not exhibit a significant amount of radioactive emission having an energy greater than 310 keV and a half life greater than about 1 day or may not exhibit a significant amount of radioactive emission having an energy greater than 100 keV and a half life greater than about 1 day. The pellet may further include one or more materials selected from aluminum, copper, vanadium, nickel, iron, titanium, silicon, carbon, oxygen, and alloys and compounds of the above combined with the ytterbium by mixing, compounding, or alloying. The pellet may be a ceramic, a glass, or a metallic wire. The pellet may be a glass fiber or a ceramic fiber. The pellet may contain sufficient unactivated $^{168}$Ytterbium to permit reactivation to an activity concentration of 20 curies/mm$^3$ or more. The pellet may contain sufficient unactivated $^{168}$Ytterbium to permit reactivation to an activity concentration of 30 curies/mm$^3$ or more.

According further to the present invention, producing a $^{169}$Ytterbium source includes preparing a pellet including ytterbium and having a volume of 2 mm$^3$ or less, and irradiating the pellet until it has an activity greater than 10 curies and an activity concentration of greater than 10 curies/mm$^3$. The pellet may include ytterbium enriched with at least 15% $^{168}$Ytterbium. The pellet may be irradiated until it has an activity concentration of at least 20 curies/mm$^3$ or at least 30 curies/mm$^3$. The pellet may have a density greater than an amount of 6 g/cm$^3$, 7 g/cm$^3$, 8 g/cm$^3$, or 9 g/cm$^3$. Preparing may include forming the pellet in the shape of a cylinder or a tube. Preparing may include sintering or hot isostatic pressing a pressed powder. Producing a $^{169}$Ytterbium source may further include encasing the pellet in a capsule. The capsule may include one or more materials selected from aluminum, copper, vanadium, nickel, iron, titanium, silicon, carbon, oxygen, and alloys and compounds of the above. Irradiating may include irradiating the encased pellet until the pellet has an activity concentration of at least 10 curies/mm$^3$. Producing a $^{169}$Ytterbium source may further include encasing the pellet in a capsule after irradiating the pellet.

According further to the present invention, preparing a $^{169}$Ytterbium radioactive source includes providing a pellet including $^{168}$Ytterbium and having a volume less than 2 mm$^3$ that has been activated to an activity greater than 10 curies and an activity concentration of greater than 10 curies/mm$^3$ and decayed by more than one half-life, and causing the pellet to be exposed to a flux of thermal neutrons of a nuclear reactor until it has an activity greater than 10 curies and an activity concentration of at least 10 curies/mm$^3$. The pellet may be irradiated until it has an activity concentration of at least 20 curies/mm$^3$ or at least 30 curies/mm$^3$. Preparing a $^{169}$Ytterbium radioactive source may further include encasing the pellet in a capsule, where encasing may be conducted before or after causing the pellet to be exposed. Preparing a $^{169}$Ytterbium radioactive source may further include removing the pellet from the capsule before causing the pellet to be exposed, and re-encapsulating the pellet after causing the pellet to be exposed.

According further to the present invention, a brachytherapy source includes a pellet including $^{169}$Ytterbium and exhibiting an activity concentration of 10 curies/mm$^3$ or more. The pellet may have a density greater than about 5 g/cm$^3$, about 6 g/cm$^3$, about 7 g/cm$^3$, about 8 g/cm$^3$, or about 9 g/cm$^3$. The pellet may have a volume less than 2 mm$^3$. The pellet may have a volume less than 1.5 mm$^3$ or less than 1 mm$^3$. The pellet may exhibit an activity concentration of at least 20 curies/mm$^3$ or at least 30 curies/mm$^3$. The brachytherapy source may further include a capsule encasing the pellet. The capsule may include one or more materials selected from of aluminum, copper, vanadium, nickel, iron, titanium, silicon, carbon, oxygen, and alloys and compounds of the above. The pellet may include powdered ytterbium or ytterbium oxide pressed into a solid form. The powdered ytterbium oxide may be formed into a pellet by sintering or hot isostatic pressing. The pellet may include ytterbium including at least 15% $^{168}$Ytterbium. The brachytherapy source may not exhibit a significant amount of radioactive emission outside a predetermined energy range. The brachytherapy source may not exhibit a significant amount of radioactive emission having an energy greater than 310 keV or may not exhibit a significant amount of radioactive emission having an energy greater than 100 keV or may not exhibit a significant amount of radioactive emission having an energy greater than 310 keV and a half life greater than about 1 day or may not exhibit a significant amount of radioactive emission having an energy greater than 100 keV and a half life greater than about 1 day. The pellet may further include one or more materials selected from aluminum, copper, vanadium, nickel, iron, titanium, silicon, carbon, oxygen, and alloys and compounds of the above combined with the ytterbium by mixing, compounding, or alloying. The pellet may be a ceramic, a glass, or a metallic wire. The pellet may be a glass fiber or a ceramic fiber.

According further to the present invention, providing brachytherapy for a patient includes providing a brachytherapy source including $^{169}$Ytterbium having an activity concentration of at least 10 curies/mm$^3$, delivering the brachytherapy source to a site in a patient for a predetermined time period, and removing the brachytherapy source from the patient. The brachytherapy source may have an activity of at least 20 curies or at least 30 curies. Providing a brachytherapy source may include providing a pellet including at least 50% ytterbium, where the ytterbium includes at least 15% $^{168}$Ytterbium, and causing the pellet to be irradiated in a neutron source. Providing brachytherapy for a patient may also include, after removing the brachytherapy source, causing at least a portion of the brachytherapy source to be exposed to a source of neutron flux until the portion has an activity concentration of at least 10 curies/mm$^3$. Providing brachytherapy for a patient may also include, after removing the brachytherapy source, causing at least a portion of the brachytherapy source to be exposed to a source of neutron flux until the portion has an activity concentration of at least 20 curies/mm$^3$. Providing brachytherapy for a patient may also include, after removing the brachytherapy source, causing at least a portion of the brachytherapy source to be exposed to a source of neutron flux until the portion has an activity concentration of at least 30 curies/mm$^3$.

BRIEF DESCRIPTION OF THE DRAWINGS

The invention is described with reference to the several figures of the drawing, in which.

DETAILED DESCRIPTION OF THE PREFERRED EMBODIMENTS

In one embodiment, the invention provides a high dose rate brachytherapy source including $^{168}$Ytterbium having a size less than 2 mm$^3$ and an activity greater than 10 curies/mm$^3$. For example, the source may include a pellet incorporating at least 50% ytterbium, at least 15% of which is $^{168}$Ytterbium. The ytterbium may be in the form of ytterbium oxide pressed into a pellet and sintered, for example, or hot isostatically pressed.

Figure 1:
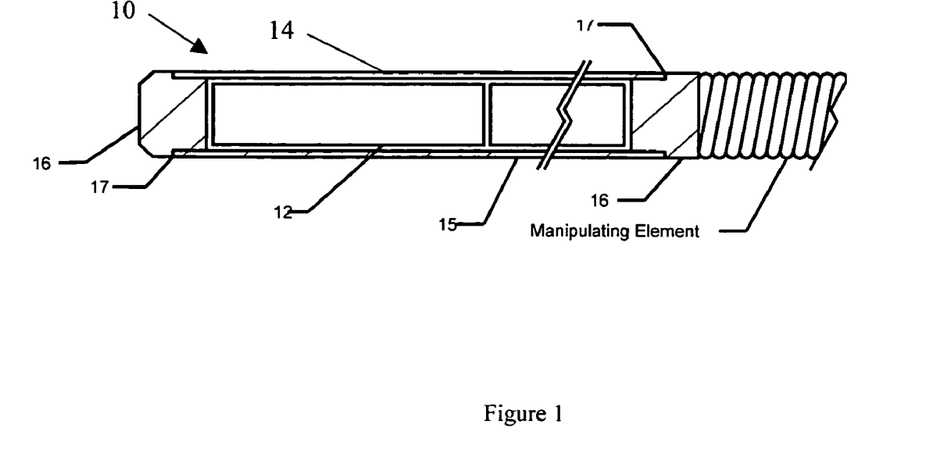
FIG. 1 is a schematic drawing of an apparatus for high dose rate brachytherapy according to an embodiment of the invention.

FIG. 1 illustrates a source 10 according to an embodiment of the invention. Source 10 is delivered to a selected site within a patient, where it emits localized X-ray and gamma radiation. The X-rays and gamma rays are emitted from one or more pellets 12 of generally cylindrical shape. One skilled in the art will recognize that the pellet may take other shapes as well, for example, a collection of spheres or some other elongated solid or tubular shape. X-ray and gamma ray-emitting $^{169}$Ytterbium material is distributed throughout each pellet. The pellets are encased and sealed within a capsule 14 formed from a half-open shell with a single cap 16 welded at one end, or from a short tube 15 with end caps 16 welded at each end, as indicated at 17.

In one embodiment, the X-ray and gamma ray-emitting material for a temporary source is ytterbium that is substantially enriched in $^{168}$Ytterbium and which has been activated (transmuted) by exposure to neutron flux to contain a fraction of X-ray and gamma ray-emitting $^{169}$Ytterbium. $^{169}$Ytterbium is a nearly ideal source of X-rays and gamma rays for temporary implantation because it has a low energy radiation spectrum, consisting primarily of low-energy X-ray emissions in the 50-65 keV range. The radiation spectrum of $^{169}$Ytterbium is softer (e.g, it is characterized by a lower energy) than the radiation spectrum of $^{192}$Iridium, the conventional radioactive isotope for high dose rate brachytherapy treatment of tumors.

Figure 2:
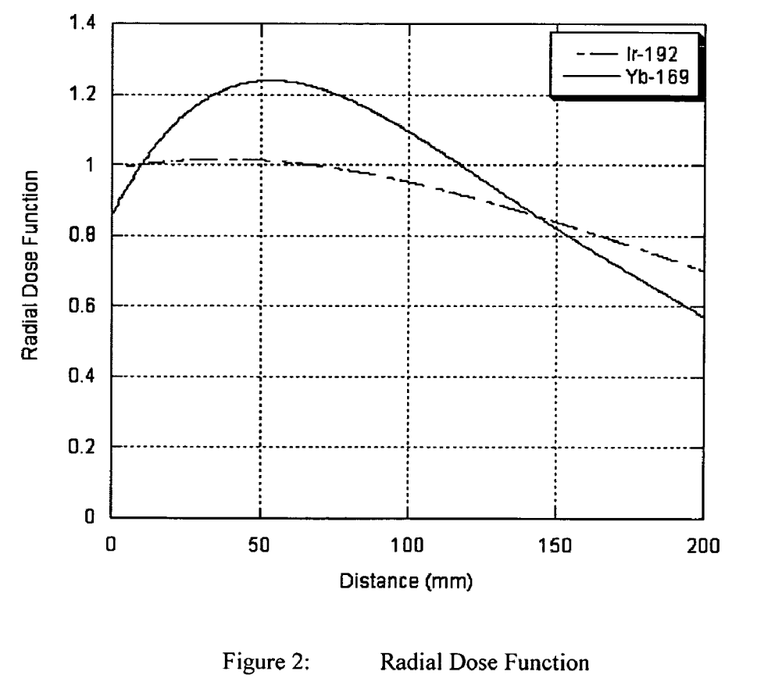
FIG. 2 is a graph comparing the radial dose function of $^{192}$Iridium and $^{169}$Ytterbium.
Figure 3:
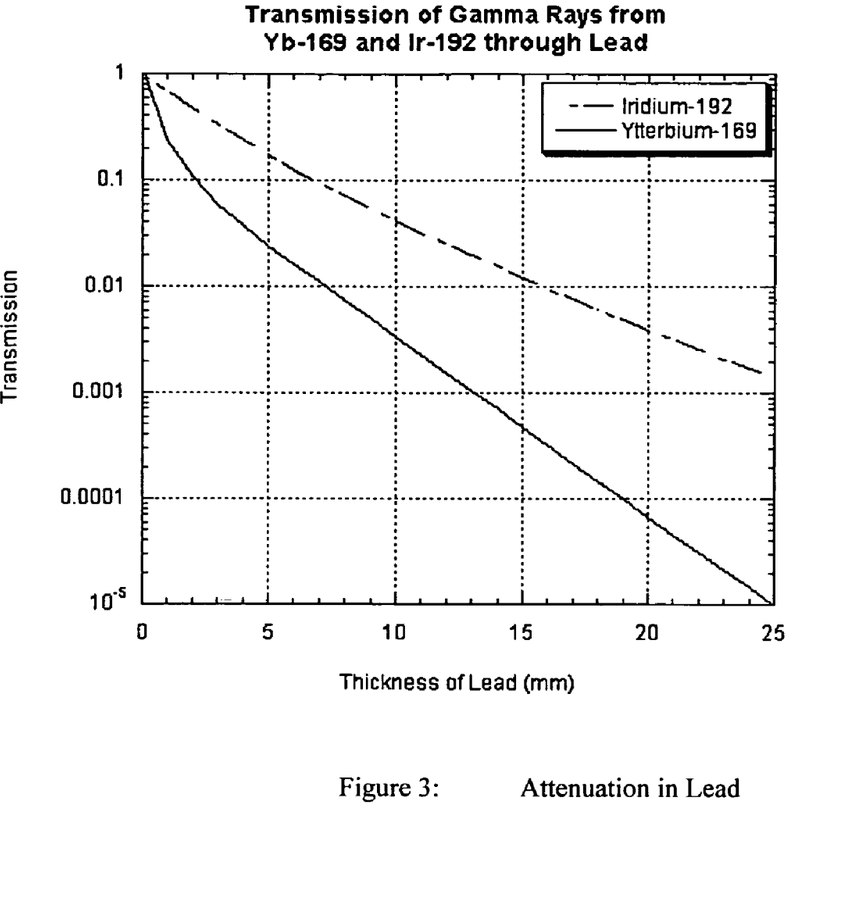
FIG. 3 is a graph comparing the transmission of gamma rays from $^{192}$Iridium and $^{169}$Ytterbium through lead.

The radiation spectrum of $^{169}$Ytterbium provides a more optimal radial dose distribution and improved shielding properties with respect to $^{192}$Iridium sources. FIG. 2 shows that the radial dose function of $^{169}$Ytterbium is higher at shorter distances but then decreases more quickly with distance than that of $^{192}$Iridium. FIG. 3 shows that a 1 cm lead barrier reduces transmission of gamma radiation from $^{169}$Ytterbium an order of magnitude more than from $^{192}$Iridium.

The advantages of $^{169}$Ytterbium have not previously been realized because of the practical difficulties involved in providing ytterbium in active form with suitable source strength to permit temporary high dose rate application to the patient at a suitable cost. Sources used to provide temporary high dose rate application to the patient may have a diameter of approximately 1 millimeter or less to suitably pass through the lumen of the treatment applicator and a length of approximately 10 millimeters or less to suitably negotiate the curvatures required to reach the treatment positions. These sources may have an activity of 10 curies or more, for example, at least 20 or at least 30 curies to provide the dose rate necessary for high dose rate brachytherapy. The cost of the source may be competitive with alternate treatment modalities.

By using ytterbium that is substantially enriched in $^{168}$Ytterbium in the manufacture of sources and then activating the $^{168}$Ytterbium in the neutron flux of a nuclear reactor to contain significant amounts of $^{169}$Ytterbium just prior to production of the sources (in a hot manufacturing process) or subsequent to production of the sources (in a cold manufacturing process), sources having a controlled amount of $^{169}$Ytterbium can be provided for treatment of a patient.

One consideration in constructing a source of $^{169}$Ytterbium is the isotopic enrichment of the ytterbium with the isotope $^{168}$Ytterbium. Naturally occurring ytterbium contains approximately 0.13 atomic percent of $^{168}$Ytterbium. Accordingly, if naturally occurring ytterbium were to be irradiated by neutron flux so as to convert this small amount of the $^{168}$Ytterbium to $^{169}$Ytterbium, the amount of natural ytterbium required to produce an X-ray and gamma ray intensity sufficient for high dose rate treatment of a patient could be of a size far in excess of what could be delivered to the treatment site. Additionally, naturally occurring ytterbium contains other isotopes, $^{174}$Ytterbium and $^{176}$Ytterbium, that, when irradiated by neutron flux, could be transmuted to other radioactive isotopes of ytterbium, $^{175}$Ytterbium and $^{177}$Ytterbium, that have less optimal radioactive properties for the treatment of a tumor or cancerous area exploiting the techniques of the invention.

In one embodiment, the source 10 emits radiation having an energy of about 50-70 keV. Beta radiation and gamma radiation having energies greater than 310 keV are less optimal for the practice of the invention. Even gamma radiation with energies greater than 100 keV will require more shielding for the technician, reducing some of the advantages provided by the use of $^{169}$Ytterbium. One skilled in the art will recognize that these energies are not contra-indicated for clinical reasons. Rather, the presence of materials that emit at higher energies negates the advantage of using low energy emitting $^{169}$Ytterbium. One skilled in the art will be able to optimize the inconvenience and expense of shielding with the expense of enriching source 10 with a given isotope of ytterbium.

Another consideration in constructing an x-ray and gamma ray source exploiting $^{169}$Ytterbium is the self-shielding effect of ytterbium. Although $^{169}$Ytterbium emits X-rays and gamma rays, all of the isotopes of ytterbium absorb substantial amounts of X-rays and gamma rays. In one embodiment, the amount of $^{169}$Ytterbium is sufficiently large to compensate for this self-shielding and provide a dose rate suitable for the temporary high dose rate treatment of a tumor. Isotopically enriched $^{169}$Ytterbium may overcome the self-shielding effect.

In one embodiment, ytterbium that is used in the temporary high dose rate brachytherapy sources is substantially enriched in $^{168}$Ytterbium. Generally, the ytterbium is enriched in $^{168}$Ytterbium to at least about 15 atomic percent and may be enriched to as much as 99 atomic percent or more, for example, to at least 20 atomic percent, at least 30 atomic percent, at least 40 atomic percent, at least 50 atomic percent, at least 60 atomic percent, at least 70 atomic percent, at least 80 atomic percent, or at least 90 atomic percent. Ytterbium can be enriched in $^{168}$Ytterbium by electromagnetic separation or by gas centrifuge separation. Ytterbium that is enriched in $^{168}$Ytterbium may be obtained from Oak Ridge National Laboratories and other suppliers.

Another consideration in constructing a source of $^{169}$Ytterbium is the density and composition of the active element of the source. An active element of reasonably high density may achieve the desired combination of size and activity. Ytterbium for use in one embodiment of the invention has a density of about 5 g/cm$^3$ or more, and the composition of the pellet is 50% or more by weight of ytterbium. In other embodiments, the density may be at least 6, at least 7, at least 8, or at least 9 g/cm$^3$, and the composition of the pellet is at least 60%, at least 70%, at least 80%, or at least 90% ytterbium.

In the X-ray and gamma ray-emitting pellets depicted in FIG. 1, enriched $^{168}$Ytterbium is distributed throughout each pellet 12. In one embodiment, pellet 12 is substantially composed of ytterbium oxide, but there is no requirement that the ytterbium be in this oxide form. The $^{168}$Ytterbium may be provided in metallic elemental form or compounded, mixed or alloyed with other elements, oxides, or other compounds. For example, the $^{168}$Ytterbium may be provided as $Yb_2O_3$, $YbF_3$, $Yb_2(C_2O_4)_3$, $Yb(NO)_3$, $Yb_3Si_5$, or some combination of these with each other or with elemental ytterbium, or in combination with other elements, oxides, or other compounds. Exemplary elements include aluminum, copper, vanadium, nickel, iron, titanium, silicon, carbon, and oxygen. One skilled in the art will recognize that compounding, mixing and alloying all facilitate fabrication of the pellets and source and even distribution of ytterbium through the pellet. In addition, if a ytterbium mixture, compound or alloy is used as the X-ray and gamma ray-emitting source, the mixture, compound or alloy may be substantially insoluble in aqueous solutions to prevent transfer of radioactive ytterbium throughout the body in the unlikely event of breach of the encapsulation and breach of the delivery catheter.

One skilled in the art will recognize how to optimize the choice and quantity of the materials to be mixed, alloyed or compounded, so that, when irradiated by neutron flux, they are not transmuted into unacceptable amounts of other radioactive isotopes that would exhibit such high levels of beta or high energy gamma radiation that the advantages of using $^{168}$Ytterbium are lost. Alternatively, the half life of such radiations may be sufficiently short that they will have inconsequential activities by the time the source is used in a patient. In one embodiment, these materials do not exhibit undesirable radiations for the treatment of tumors, e.g., they do not exhibit significant radioactive emission outside the energies exhibited by $^{169}$Ytterbium emissions, either because they do not exhibit such emissions or because they only exhibit such emissions for a short time, such that the amount of such emissions is inconsequential shortly after irradiation.

For example, in one embodiment, the pellet is irradiated by a third party in a reactor. The reactor may require some time, even as much as a day, to cool before the pellet can be recovered and sent to a supplier or a hospital. Even overnight shipping requires close to 24 hours. If a supplier is providing the source to a hospital, for example, if the irradiated pellet requires encapsulation, another day may be required to get the source from the supplier to the hospital. As a result, even if irradiated non-Yb materials in the source have half-lives on the order of a day, the level of emitted radiation will decrease by half in one day and by 88% in three days. For a half life of 16 hours, the level of radiation after two days will only be 12.5% of the level immediately after irradiation.

In one embodiment, enriched ytterbium oxide, either alone or combined with other materials as discussed above, is provided in powder form having average particle sizes of between about 20 and about 200 microns. The powder is pressed into a cylinder at pressures sufficient to achieve at least about 75% of theoretical density, for example, 90,000 psi (620 MN/m$^2$). In another method, the pressed cylinder is sintered by heating to a high temperature, for example 2,000° C., to bind the particles of powder together and increase the density to about 95% of theoretical density. Alternatively, hot isostatic pressing (HIP) may be used to form the pellet. In another embodiment, enriched metallic ytterbium, either alone or with other materials, is drawn into solid wire. In another embodiment, ytterbium oxide, either alone or with other oxides, glass forming compounds, or elements, is formed into a glass and drawn into fiber. Those skilled in the art will recognize that various metallurgical and ceramics fabrication techniques may be used to produce pellets for use with the invention.

One advantage of using ytterbium enriched in $^{168}$Ytterbium is its ability to be activated by a high neutron flux to produce $^{169}$Ytterbium. $^{168}$Ytterbium transmutes to $^{169}$Ytterbium through neutron capture. A common source of high neutron flux is a radiation beam from a nuclear reactor. Because a reactor emits a mixture of radiation types, it may be desirable to use appropriate filters to enhance the neutron flux spectrum.

The techniques described herein may be exploited to produce a source of $^{169}$Ytterbium whose cost is competitive with alternate treatment modalities. The amount of ytterbium in a pellet depends upon the radiation dosage required for each source. For suitability for delivery to a tumor, the source may be as small as possible and yet exhibit a dose rate sufficient to provide the desired treatment dose within a period of less than one hour.

The cost of ytterbium enriched in the isotope 168Ytterbium is very expensive. The US Department of Energy sells ytterbium enriched in the isotope $^{168}$Ytterbium at a cost of $427/mg. A source with a density of 5 g/cm$^3$ and a volume of 2 mm$^3$ would have a mass of 10 mg and cost $4,270. This is far more costly than the conventional $^{192}$Iridium source. However, the techniques described herein may be exploited to produce a source with the appropriate enrichment, density and size to achieve a number of $^{168}$Ytterbium atoms such that only a small fraction of these need be activated to achieve the desired activity of 10 curies. One skilled in the art will recognize that smaller, e.g., 1.5 mm , 1 mm , or even less, or larger sources may be employed. The size of the source should be optimized for the delivery apparatus and for the amount of radiation delivery desired. Of course, a plurality of sources may be employed simultaneously. In addition, the pellet can be re-activated after decay, for example, after one or two half lives, to achieve the desired initial activity. Multiple activations of the same $^{169}$Ytterbium pellet allows the high material cost to be amortized over multiple uses, resulting in a cost comparable to the encapsulated $^{192}$Iridium source.

In one embodiment, the pellets 16 are encapsulated to prevent direct contact of the radioactive material with human tissue. For example, each pellet may be plated or coated to form a capsule of nonradioactive material surrounding the pellet. Alternatively, or in addition, pellet 16 may be sealed in a capsule 14 as described above. The encapsulation materials should not exhibit significant low energy X-ray absorption. It is further desirable that the outer shell be biocompatible in the unlikely event of breach of the delivery catheter.

$^{168}$Ytterbium activation may be performed either after the source is fully assembled, e.g., in a cold process, or just before the source is finally assembled, e.g., in a hot process. The cold process simplifies the manufacturing process of the source—no precautions against radiation exposure are necessary during assembly because the source becomes radioactive only after final assembly. In a cold process, activation is the final step, and the sources can be used almost immediately, before substantial amounts of the $^{169}$Ytterbium have decayed. However, even using a hot process, where activation is performed on the ytterbium pellets prior to their final assembly into the sources, the final source assembly may be performed relatively quickly, allowing the sources to be provided at or near maximum $^{169}$Ytterbium activity. Although a hot process requires apparatus for shielding technicians who assemble the sources from radioactivity, the hot process has the advantage of substantially removing concerns about transmutation of isotopes present in other components of the source, such as the capsule or the manipulating components, because these are not exposed to any neutron radiation flux. Thus, when a hot process is used, the materials for capsule 14 may be selected without regard to the transmutability of isotopes that may be present, either as a major component or as impurities.

The cold manufacturing of ytterbium sources involves irradiation of the source after the components are assembled and welded. As a result, the capsule is also irradiated. Commercially available materials contain trace impurities that are activated by the neutron field of a nuclear reactor. The neutrons also activate the structural materials themselves. Consequently, the capsule components may be fabricated from materials that do not contain unacceptable amounts of isotopes that, when irradiated by neutron flux, could be transmuted to radioactive isotopes that emit radiations undesirable for the treatment of tumors, or if transmuted into radioactive isotopes that emit undesirable radiations, have such short half-lives that they will have inconsequential activities shortly after irradiation. Exemplary suitable materials include aluminum, copper, vanadium, nickel, iron and silicon. Where the capsule material is not biocompatible, an additional outermost shell fabricated from a biocompatible material may be deployed around the inner shell after irradiation.

It may be useful to coordinate source manufacture with patient treatment scheduling. Although sources can be used at any time, depending on the residual $^{169}$Ytterbium activity, it is impractical to use sources in which the $^{169}$Ytterbium has decayed to a very low percent of initial activity in place of a freshly activated source because the treatment time will be too long. The activity of $^{169}$Ytterbium may be computed from the natural decay period of the isotope. Due to the cost of $^{168}$Ytterbium-enriched ytterbium, the sources are relatively expensive to produce, and it is preferred to reactivate sources that have decayed to too low an activity.

After a certain period of decay, the treatment center may return the sources to the manufacturer for reactivation. Because $^{168}$Ytterbium content will not have been significantly diminished, reactivated sources could have essentially the same activity as newly manufactured sources. As long as the source is manufactured of materials that do not contain unacceptable amounts of isotopes that transmute to undesirable radioactive isotopes, this ability to reactivate sources containing $^{168}$Ytterbium-enriched ytterbium is a significant advantage that the techniques described herein provide to clinicians and patients.

Of course, if sources have been manufactured by a hot process so that the source components were selected without regard for their isotope content, the assembled sources may not be so easily reactivated. Nevertheless, the pellets may be removed from the sources, reactivated and used to remanufacture additional sources. The mere ability to reactivate $^{168}$Ytterbium-enriched ytterbium still represents an advantage of ytterbium relative to other radionuclides used for this purpose.

The ytterbium source has many inherent benefits for the patient. The small size of the ytterbium sources permit delivery to the treatment site with a minimum of tissue trauma. The sources may be delivered through a small diameter catheter. The $^{169}$Ytterbium isotope was selected because of its soft therapeutic X-rays and gamma rays. This energy range provides a favorable dose distribution to the surrounding tumor. The low energy X-rays and gamma rays benefit the patient and staff due to the simplified radiation protection requirements, which may eliminate the need for expensive isolated heavily shielded facilities. Low energy X-rays and gamma rays may be adequately shielded by a relatively thin (~1 cm) amount of lead. Thin metal shields and lead glass shields are commercially available to provide protection for the technicians preparing the $^{169}$Ytterbium sources for delivery. When reasonable precautions are taken, e.g., handling sources with forceps and/or remote handling devices and using thin lead shields, medical personnel can expect to receive very little exposure. In the unlikely event that a $^{169}$Ytterbium source capsule and/or delivery catheter ruptures, the biologically inert components of the source represent little or no toxicity danger to the patient.

Because the pellets are encapsulated in a non-toxic shell, any toxic effects of the base material may generally be ignored. Even in the rare event that a breach of the shell and the delivery catheter allowing body fluids to gradually seep into the shell, there would be very slow transfer of any dissolved base material from the breached shell. Sources to be delivered should receive microscopic inspection and should be tested for leaks of the shell before shipment to ensure that the shell will not be breached during use. Some embodiments of the invention employ sources that have the further advantage of being similar in size and shape to the sources presently used to administer high dose rate $^{192}$Iridium, and therefore, should readily gain acceptance by both government regulators and users, e.g., physicians.

Figure 4:
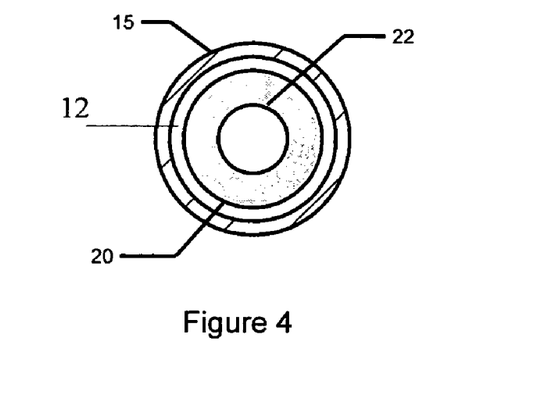
FIG. 4 is a cross-sectional view of a source for high dose rate brachytherapy according to an embodiment of the invention.

Although the uniform solid pellet form of ytterbium represents one exemplary mode of administration, the ytterbium may be administered in other forms. Illustrated in FIG. 4 is a pellet 12 that has several of the advantages of the source described above. In this embodiment, $^{168}$Ytterbium-enriched ytterbium is distributed as an outer layer 20 over the surface of a core 22 of other low-absorbing material, such as aluminum, quartz or air (e.g, a hollow or tubular source or pellet). The outer layer serves as an X-ray marker for external visualization, and the distribution of a small amount of $^{168}$Ytterbium-enriched ytterbium over the surface of the core makes efficient use of the expensive enriched ytterbium and provides a very uniform distribution of emitted X-rays. In this case, the quantity of enriched $^{168}$Ytterbium per unit volume is reduced, but the self-absorption of the emitted x-rays and gamma rays is also reduced.

Ytterbium and ytterbium oxide are also x-ray opaque and allow visualization of the source with an external x-ray apparatus after the source has been deployed to the treatment position, eliminating the need for an additional marker. Other methods of visualizing internal organs and materials are coming into increasing use, including computed tomographic scanning and magnetic resonance imaging scanning. If visualization of the tumor and the sources therein is contemplated by method other than X-ray, the source may include a marker particularly adapted for visualization by that technique.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is

1. A $^{169}$Ytterbium radioactive source to be used for temporary brachytherapy which is encapsulated prior to activation in a material that does not contain unacceptable amounts of isotopes that, when irradiated by neutron flux, would be transmuted to radioactive isotopes that emit undesirable radiations for the treatment of tumors, or if transmuted into radioactive isotopes that emit undesirable radiations, have such short half-lives that they will have inconsequential activities shortly after irradiation, wherein the $^{169}$Ytterbium radioactive source has an activity greater than 10 curies, has an activity concentration of at least 10 curies/mm$^3$, has a density of at least 5 g/cm$^3$, has a composition that is at least 50% by weight of ytterbium, and does not exhibit a significant amount of radioactive emission having an energy greater than 310 keV.

2. A $^{169}$Ytterbium radioactive source, comprising:
a pellet having a size of 2 mm$^3$ or less, wherein said pellet includes ytterbium and has an activity greater than 10 curies and an activity concentration of at least 10 curies/mm$^3$, wherein the pellet has a density of at least 5 g/cm$^3$, wherein a composition of the pellet includes at least 50% by weight of the ytterbium, and wherein the pellet does not exhibit a significant amount of radioactive emission having an energy greater than 310 keV.

3. The source of claim 2, further including a capsule encasing said pellet.

4. The source of claim 2, wherein said ytterbium includes at least 15% $^{168}$Ytterbium.

5. The source of claim 2, wherein the pellet includes ytterbium oxide enriched with at least 15% $^{168}$Ytterbium oxide and wherein the source includes a biocompatible capsule encasing said pellet.

6. The source of claim 2, wherein said pellet has a density of at least an amount selected from 6 g/cm$^3$, 7 g/cm$^3$, 8 g/cm$^3$, and 9 g/cm$^3$.

7. The source of claim 2, wherein said source has an activity concentration of at least 20 curies/mm$^3$.

8. The source of claim 7, wherein said source has an activity concentration of at least 30 curies/mm$^3$.

9. A $^{169}$Ytterbium radioactive source, comprising:
a pellet including ytterbium, the ytterbium including $^{168}$Ytterbium, and having a volume less than 2 mm$^3$, wherein said pellet, having once been activated to an activity greater than 10 curies and an activity concentration of greater than 10 curies/mm$^3$ and decayed by more than one half-life, contains sufficient remaining unactivated $^{168}$Ytterbium to permit reactivation to an activity greater than 10 curies, and an activity concentration of greater than 10 curies/mm$^3$ by exposure to a flux of thermal neutrons of a nuclear reactor, wherein the pellet has a density of at least 5 g/cm$^3$, wherein a composition of the pellet includes at least 50% by weight of the ytterbium, and wherein the pellet does not exhibit a significant amount of radioactive emission having an energy greater than 310 keV.

10. The source of claim 9, wherein said ytterbium includes at least 15% $^{168}$Ytterbium.

11. The source of claim 9, wherein said pellet has a density greater than an amount selected from 5 g/cm$^3$, 6 g/cm$^3$, 7 g/cm$^3$, 8 g/cm$^3$, and 9 g/cm$^3$.

12. The source of claim 9, wherein said pellet has a volume of an amount selected from at most 1.5 mm$^3$ and at most 1 mm$^3$.

13. The source of claim 9, wherein said pellet includes powdered ytterbium or ytterbium oxide pressed into a solid form.

14. The source of claim 13, wherein said powdered ytterbium oxide is formed into a pellet by sintering or hot isostatic pressing.

15. The source of claim 9, wherein said ytterbium is in an amount selected from at least 60%, at least 70%, at least 80%, and at least 90%.

16. The source of claim 15, wherein said ytterbium includes $^{168}$Ytterbium in an amount selected from at least 20%, at least 30%, at least 40%, at least 50%, at least 60%, at least 70%, at least 80%, and at least 90%.

17. The source of claim 9, further including a capsule encasing said pellet.

18. The source of claim 17, wherein said capsule does not exhibit a significant amount of radioactive emission outside a predetermined energy range.

19. The source of claim 18, wherein said capsule does not exhibit a significant amount of radioactive emission having an energy greater than 100 keV.

20. The source of claim 18, wherein said capsule does not exhibit a significant amount of radioactive emission having an energy greater than 310 keV and a half life greater than about 1 day.

21. The source of claim 20, wherein said capsule does not exhibit a significant amount of radioactive emission having an energy greater than 100 keV and a half life greater than about 1 day.

22. The source of claim 17, wherein said capsule includes one or more materials selected from aluminum, copper, vanadium, nickel, iron, titanium, silicon, carbon, oxygen, and alloys and compounds of the above.

23. The source of claim 17, wherein said source, when irradiated by a neutron flux, does not exhibit a significant amount of radioactive emission outside a predetermined energy range.

24. The source of claim 9, wherein said source, when irradiated by a neutron flux, does not exhibit a significant amount of radioactive emission having an energy greater than 310 keV.

25. The source of claim 24, wherein said source, when irradiated by a neutron flux, does not exhibit a significant amount of radioactive emission having an energy greater than 100 keV.

26. The source of claim 9, wherein said source, when irradiated by a neutron flux, does not exhibit a significant amount of radioactive emission having an energy greater than 310 keV and a half life greater than about 1 day.

27. The source of claim 26, wherein said source, when irradiated by a neutron flux, does not exhibit a significant amount of radioactive emission having an energy greater than 100 keV and a half life greater than about 1 day.

28. The source of claim 9, wherein said pellet further includes one or more materials selected from aluminum, copper, vanadium, nickel, iron, titanium, silicon, carbon, oxygen, and alloys and compounds of the above combined with said ytterbium by mixing, compounding, or alloying.

29. The source of claim 9, wherein said pellet is a ceramic, a glass, or a metallic wire.

30. The source of claim 29, wherein said pellet is a glass fiber or a ceramic fiber.

31. The source of claim 9, wherein said pellet contains sufficient unactivated $^{168}$Ytterbium to permit reactivation to an activity concentration of 20 curies/mm$^3$ or more.

32. The source of claim 9, wherein said pellet contains sufficient unactivated $^{168}$Ytterbium to permit reactivation to an activity concentration of 30 curies/mm$^3$ or more.

33. A brachytherapy source, comprising:
a pellet including ytterbium, the ytterbium including $^{169}$Ytterbium, and exhibiting an activity concentration of 10 curies/mm$^3$ or more, wherein the pellet has a density of at least 5 g/cm$^3$, wherein a composition of the pellet includes at least 50% by weight of the ytterbium, and wherein the pellet does not exhibit a significant amount of radioactive emission having an energy greater than 310 keV.

34. The brachytherapy source of claim 33, wherein said pellet has a density greater than at least one of: about 6 g/cm$^3$, about 7 g/cm$^3$, about 8 g/cm$^3$, and about 9 g/cm$^3$.

35. The brachytherapy source of claim 33, wherein said pellet has a volume less than 2 mm$^3$.

36. The brachytherapy source of claim 35, wherein said pellet has a volume less than 1.5 mm$^3$.

37. The brachytherapy source of claim 36, wherein said pellet has a volume less than 1 mm$^3$.

38. The brachytherapy source of claim 33, wherein the pellet exhibits an activity concentration of at least 20 curies/mm$^3$.

39. The brachytherapy source of claim 38, wherein the pellet exhibits an activity concentration of at least 30 curies/mm$^3$.

40. The brachytherapy source of claim 33, further including a capsule encasing said pellet.

41. The brachytherapy source of claim 40, wherein said capsule includes one or more materials selected from of aluminum, copper, vanadium, nickel, iron, titanium, silicon, carbon, oxygen, and alloys and compounds of the above.

42. The brachtherapy source of claim 33, wherein said pellet includes powdered ytterbium or ytterbium oxide pressed into a solid form.

43. The brachytherapy source of claim 42, wherein said powdered ytterbium oxide is formed into a pellet by sintering or hot isostatic pressing.

44. The brachytherapy source of claim 33, wherein said ytterbium includes at least 15% $^{168}$Ytterbium.

45. The brachytherapy source of claim 33, wherein said source does not exhibit a significant amount of radioactive emission outside a predetermined energy range.

46. The brachytherapy source of claim 33, wherein said source does not exhibit a significant amount of radioactive emission having an energy greater than 100 keV.

47. The brachytherapy source of claim 33, wherein said source does not exhibit a significant amount of radioactive emission having an energy greater than 310 keV and a half life greater than about 1 day.

48. The brachytherapy source of claim 47, wherein said source does not exhibit a significant amount of radioactive emission having an energy greater than 100 keV and a half life greater than about 1 day.

49. The brachytherapy source of claim 33, wherein said pellet further includes one or more materials selected from aluminum, copper, vanadium, nickel, iron, titanium, silicon, carbon, oxygen, and alloys and compounds of the above combined with said ytterbium by mixing, compounding, or alloying.

50. The brachytherapy source of claim 33, wherein said pellet is a ceramic, a glass, or a metallic wire.

51. The brachytherapy source of claim 50, wherein said pellet is a glass fiber or a ceramic fiber.

* * * * *